United States Patent
Peterson

(10) Patent No.: US 6,294,350 B1
(45) Date of Patent: *Sep. 25, 2001

(54) METHODS FOR TREATING FIBROPROLIFERATIVE DISEASES

(75) Inventor: Theresa C. Peterson, Nova Scotia (CA)

(73) Assignee: Dalhousie University, Halifax (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/433,621

(22) Filed: Nov. 2, 1999

Related U.S. Application Data

(63) Continuation-in-part of application No. 09/092,317, filed on Jun. 5, 1998, now Pat. No. 6,025,151, which is a continuation-in-part of application No. 08/870,096, filed on Jun. 5, 1997, now Pat. No. 5,985,592.

(51) Int. Cl.[7] .............................. C12Q 1/02; C12Q 1/00; C12Q 1/50

(52) U.S. Cl. ................... 435/29; 435/975; 435/4; 435/17; 424/9.1; 424/277.1; 424/553; 424/551

(58) Field of Search ................ 435/29, 975, 4, 435/17; 424/9.1, 277.1, 553, 551

(56) References Cited

U.S. PATENT DOCUMENTS

| | | | |
|---|---|---|---|
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 5,585,380 | 12/1996 | Bianco et al. | 435/29 |
| 5,985,592 | * 11/1999 | Peterson | 435/29 |
| 6,025,151 | * 2/2000 | Peterson | 435/29 |

FOREIGN PATENT DOCUMENTS

| | | |
|---|---|---|
| 36 04 149 A1 | 8/1987 | (DE) . |
| 0 544 391 A1 | 6/1993 | (EP) . |
| 87 00523 A2 | 1/1987 | (WO) . |
| 92 19772 A1 | 11/1992 | (WO) . |
| 95 02051 A2 | 1/1995 | (WO) . |
| 95 26727 A1 | 10/1995 | (WO) . |

OTHER PUBLICATIONS

Bamberger, et al., "Modulation of AP–1 activity by the human progesterone receptor in endometrial adenocarcinoma cells" *Proc. Natl. Acad. Sci. USA* 93:6169–6174 (1996).

Bessler, et al., "Effect of Pentoxifylline on the Phagocytic Acvitit, cAMP Levels, and Superoxide Anion Production by Monocytes and Polymorphonuclear Cells" *J. Leukocyte Biol.* 40:747–754 (1986).

(List continued on next page.)

Primary Examiner—Louise N. Leary
(74) Attorney, Agent, or Firm—Foley & Lardner; Stephen E. Reiter

(57) ABSTRACT

In accordance with the present invention, fibroproliferative disease or condition characterized by such symptoms as increased levels of c-Jun homodimers, increased heterodimerization of c-Jun with another signaling peptide, increased levels of phosphorylated c-Jun, or increased presence of Jun kinase are treated by administering to the subject an amount of a compound effective to ameliorate one or more of the symptoms of the disease or condition, for example, an antiproliferative or antifibrotic agent. Preferred compounds for administration according to the invention are antisense c-Jun oligonucleotides and compounds that block c-Jun phosphorylation, such as pentoxifylline, or a functional derivative or metabolite thereof. Also provided by the present invention are in vitro tests for identifying whether a test compound is useful for treatment of a subject afflicted with such a disease and kits useful for conducting such assays.

42 Claims, 1 Drawing Sheet

Effect of pentoxifylline on phosphoser73 cJun positive immunoreactivity in wt c-jun transfected PC12ES cells

OTHER PUBLICATIONS

Bogoyevitch, et al., "Cellular Stresses Differentially Activate c–Jun N–terminal Protein Kinases and Extracellular Signal–regulated Protein Kinases in Cultured Ventricular Myocytes" *J. Biol. Chem.* 270(50):29710–17 (1995).

Buchdunger, et al., "Inhibition of the Abl Protein–Tyrosine Kinase in Vitro and in Vivo by a 2–Phenylaminopyrimidine Derivative" *Cancer Res.* 56:100–4 (1996).

Burgering, et al., "cAMP antagonizes p21$^{ras}$–directed activation of extracellular signal–regulated kinase 2 and phosphorylation of mSos nucleotide exchange factor" *The EMBO Journal* 12(11):4211–4220 (1993).

Cimminiello et al., "Platelet–Derived Growth Factor (PDGF) in Patients with Different Degrees of Chronic Arterial Obstructive Disease" *Angiology* 45(4):289–293 (1994).

Coso, et al., "Transforming G Protein–coupled Receptors Potently Activate JNK (SAPK)" *J. Biol. Chem.* 270(10):5620–5624 (1995).

Crespo, et al., "Signaling through Transforming G Protein–coupled Receptors in NIH 3T3 Cells Involves c–Raf Activation" *J. Biol. Chem.* 269(33):21103–21109 (1994).

Davis, "The Mitogen–activated Protein Kinase Signal Transduction Pathway" R.J. *J. Biol. Chem.* 268(20):14553–14556 (1993).

Dohlman, et al. "Generation of a unique fibroblast–activating factor by human monocytes" *Immunol.* 52:577–584 (1984).

Gesualdo, et al., "Platelet–Derived Growth Factor Expression in Mesangial Proliferative Glomerulonephritis" *Lab Invest.* 65(2):160–167 (1991).

Herschman, H. R., "Primary Response Genes Induced by Growth Factors and Tumor Promoters"0 *Ann. Rev. of Biochem.* 60:281–319 (1991).

Hunter and Karin, "The Regulation of Transcription by Phosphorylation" *Cell* 70:375–387 (1992).

Imai, et al., "Effect of growth factors on hyaluronan and proteoglycan synthesis by retroocular tissue fibroblasts of Graves' opthalmopathy in culture" *Acta Endocrinologica* 126:541–552 (1992).

Kuratsu, et al, "Antiproliferative effect of trapidil, a platelet-derived growth factor antagonist, on a glioma cell line in virto" *J. Neurosurg.* 73:436–440 (1990).

Lo, et al., "Reactive Oxygen Species Mediate Cytokine Activation of c–Jun $NH_2$–terminal Kinases*" *J. Biol. Chem.* 271(26):15703–15707 (1996).

Leon and Rojkind, "A Simple Micromethod for Collagen and Total Protein Determination in Formalin–fixed Paraffin–embedded Sections[1,2]" *J. Histochem. and Cytochem.* 33(8):737–743 (1985).

Luke and Rocci, "Determination of pentoxifylline and a major metabolite, 3,7–demethyl–1–(5'–hydroxyhexy)xanthine, by high–performance liquid chromatography" *J. Chromatogr.* 374(1):191–195 (1986).

Marra, et al., "Involvement of phosphatidylinositol 3–kinase in the activation of extracellular signal–regulated kinase by PDGF in hepatic stellate cells" *FEBS Lett.* 376:141–145 (1995).

McCormick, F., "How receptors turn Ras on" *Nature* 363:15–16 (1993).

Meskini et al., "Phosphodiesterase Inhibitory Profile of Some Related Xanthine Derivatives Pharmacologically Active on the Peripheral Microcirculation" *Biochem. Pharmacol.* 47(5):781–788 (1994).

Nakamura, et al., "Renal Platelet–Derived Growth Factor Gene Expression in NZB/W F1 Mice with Lupus and ddY Mice with IgA Nephropathy" *Clin. Immunol. Immunopathol.* 63(2):173–181 (1992).

Palech, S.L., "Networking with protein kinases" *Curr. Biol.* 3(8):513–515 (1993).

Pesonen, E., "Infection and intimal thickening: evidence from coronary arteries in children" *Eur. Heart J.* 15(Suppl X):57–61 (1994).

Peterson, "Interleukin–1, platelet derived growth factor, free radicals and monocyte aryl hydrocarbon hydroxylase activity in liver disease. Role of cell communication" *Biochem. Pharmacol.* 43(5):1163–1166 (1992).

Peterson, T. C., "Pentoxifylline Prevents Fibrosis in an Animal Model and Inhibits Platelet–derived Growth Factor–driven Proliferation of Fibroblasts" *Hepatol.* 17(3):486–493 (1993).

Peterson, T.C. "Inhibition of Fibroproliferation by Pentoxifylline Activity of Metabolite–1 and Lack of Role of Adenosine Receptors" *Biochem. Pharmacol.* 52:597–602 (1996).

Peterson and Isbrucker, "Fibroproliferation in Liver Disease: Role of Monocyte Factors" *Hepatol.* 15(2):191–197 (1992).

Peterson and Neumeister, "Effect of pentoxifylline in rat and swine models of hepatic fibrosis: role of fibroproliferation in its mechanism" *Immunopharmacol.* 31:183–193 (1996).

Peterson and Tanton, "Effect of Pentoxifylline in Collagenous Colitis" *Can. J. Gastroenterol.* 10:S76 (1996).

Peterson et al., "In vitro effect of platelet–derived growth factor on fibroproliferation and effect of cytokine antagonists" *Immunopharmacol.* 28:259–270 (1994).

Pietrogrande, et al., "A Role for Platelet–Derived Growth Factor in Drug–Induced Chronic Ergositm? A Case Report" *Angiology* 46(7):633–636 (1995).

Rosenwald, et al., "Transient inhibition of protein synthesis induces expression of protooncogenes and stimulates resting cells to enter the cell cycle" *Cell Prolif.* 28:631–644 (1995).

Schafer, et al., "PACAP Stimulates Transcription of c–Fos and c–Jun and Activates the P–1 Transcription Factor in Rat Pancreatic Carcinoma Cells" *Biochem. Biophys. Res. Commun.* 221:111–116 (1996).

Schlesinger, J., "How receptor tyrosine kinases activate Ras" *Trends Biochem. Sci.*, 18:273–275 (1993).

Shaw, et al., "Pathogenesis of Pulmonary Fibrosis in Interstitial Lung Disease" *Am. Rev. Respir. Dis.* 143:167–173 (1991).

Terano, et al., "Eicosapentaenoic Acid Suppressed the Proliferation of Vascular Smooth Muscle Cells Through Modulation of Various Steps of Growth Signals" *Lipids* 31:S301–S304 (1996).

Uebelhoer, et al., "Modulation of Fibroblast Activity in Histiocytosis X by Platelet–Derived Growth Factor" *Chest* 107:701–705 (1995).

Wu et al., "Inhibition of the EGF–Activated Map Kinase Signaling Pathway by Adenosine 3',5'–Monophosphate" *Science* 262:1065–1069 (1993).

Xie and Herschan, "v–src Induces Prostaglandin Synthase 2 Gene Expression by Activation of the c–June N–terminal Kinase and the c–June Transcroption Factor*" *J. Biol. Chem.* 270:27622–27628 (1995).

Yoshida, et al., "Involvement of Interleukin–8, Vascular Endothelial Growth Factor, and Basic Fibroblast Growth Factor in Tumor Necrosis Factor Alpha–Dependent Angiogenesis" *Molecular and Cellular Biology* 17(7):4015–4023 (1997).

Zar, J.H. in Biostatistical methods. Prentice–Hall (Englewood Cliffs, N.J., 1974).

Patent Abstracts of Japan vol. 098, No., 008, Jun. 30, 1998 & JP 10 067661 A (Hoechst Yakyhin Kogyo KK), Mar. 10, 1998 see abstract & JP 10 067661 A (Hoechst Yakuhin Kogyo KK) Mar. 10, 1998 see abstract (1–4,8,9).

FR 2 531 337 A (Hoechst Lab) Feb. 10, 1984 see p. 1, line 4–line 13 (1–4,8,9).

YaoAO–Ping et al.: "effect of curcumin on 12–o–tetradecanoylphorbol–13–acetate and ultraviolet light–induced expression of c–jun and c–fos in JB6 cells and in mouse epidermis" *Carcinogenesis*, vol. 15, No. 10, 1994, pp. 2363–2370 XP002084271 (1–3).

Williams et al: "pentoxifylline modifies cytokine gene expression in bleomycin–injured rates lungs" *Clinical Research*, vol. 41, No. 1, 1993, p. 54a XP002084272 see abstract (1–4).

Giri et al: "differential expression of c–jun and c–myc in n–nitroso hepatic oncogenesis in akr mice" *Cancer Letters*, vol. 109, No. 1–2, 1996, pp. 121–127, XP002084274 see abstract,k last sentence (1,2).

Welsh et al: "effects of pentoxifylline on endotoxin–induced lung neutrophil sequestration and extravasuclular protein accumulation in the dog" *Respir Dis*, vol. 137, No. 4, 1988, p. 144 XP002084275 see abstract (15–17,20,21).

* cited by examiner

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: antisense c-jun oligonucleotide

<400> SEQUENCE: 1
gcagtcatag aacagtccgt cacttcacgt                    30

METHODS FOR TREATING FIBROPROLIFERATIVE DISEASES

RELATED APPLICATIONS

This application is a continuation-in-part of U.S. Ser. No. 09/092,317, filed Jun. 5, 1998, now U.S. Pat. 6,025,151, which is a continuation-in-part of U.S. Ser. No. 08/870,096, filed Jun. 5, 1997, now U.S. Pat. No. 5,985,592, the entire contents of each of which is hereby incorporated by reference herein.

FIELD OF THE INVENTION

The present invention relates to methods for treatment of disease and particularly to methods for treating diseases characterized by undesirable levels of phosphorylation of c-Jun.

BACKGROUND OF THE INVENTION

Collagenous colitis was first described by Lindstrom as chronic watery diarrhea (*Pathol Eur* 11(1):87–89, 1976). Collagenous colitis is characterized by collagen deposition, likely resulting from an imbalance between collagen production by mucosal fibroblasts and collagen degradation. Very little is understood, however, regarding the mechanism by which collagenous colitis results in secretory diarrhea.

The incidence of collagenous colitis is similar to primary biliary cirrhosis. This disease has an annual incidence of 1.8 per 100,000 and a prevalence of 15.7 per 100,000, which is similar to primary biliary cirrhosis (12.8 per 100,000) and lower than ulcerative colitis (234 per 100,000), Crohn's disease (146 per 100,000) or celiac disease (5 per 100,000). In patients with chronic diarrhea, about 0.3 to 5% have ollagenous colitis.

In efforts to characterize the patients under study, sera and monocyte conditioned media (MCM) from patients with collagenous colitis have been assessed for their ability to stimulate fibroproliferation. Cytokine antibodies were used to characterize the fibroproliferative component of patient samples.

Previous studies have suggested that MCM samples obtained from patients with liver disease are capable of stimulating proliferation of fibroblasts (see Peterson and Isbrucker, in *Hepatol.* 15(2):191–197, 1992). It has also been established that several genes involved in proliferation possess AP-1 binding sites, and thus would be expected to be susceptible to regulation by the immediate early genes c-fos and c-jun (see, for example, Schafer et al., in *Biochem Biophys Res Commun* 221:111–116, 1996) and Bamberger et al., in *Proc Nat Acad Sci. USA* 9:6169–6174, 1996).

In order to determine whether these immediate early genes are upregulated by MCM obtained from patients with liver disease, the effect of MCM from patients with liver disease was investigated. MCM exerts many effects due to PDGF (see, for example, Peterson and Isbrucker, supra, 1992) and Peterson and Tanton in *Can. J. Gastroenterol.* 10:S76 1996)). Indeed, it has been established that PDGF itself stimulates proliferation of fibroblasts (see T. C. Peterson, in *Hepatol.* 173):486–493, 1993) and Peterson et al., in *Immunopharmacol.* 28:259–270, 1994). Thus, the question of whether PDGF upregulates the expression of c-fos and c-jun was addressed.

Prior studies have indicated that pentoxifylline inhibits PDGF and MCM stimulated proliferation (see, for example, T. C. Peterson, supra, 1993), Peterson et al., in *Immunopharmacol.* 28:259–270, 1994) and Peterson and Neumeister in *Immunopharmacol.* 31:183–193, 1996)). The mechanism for this effect of pentoxifylline remains unclear, but does not appear to involve competing for the PDGF receptor or adenosine receptor activation (see T. C. Peterson, in *Biochem Pharmacol* 52:597–602, 1996)).

It is known that c-Jun forms heterologous signaling protein combinations with a number of entities. For instance, c-Jun forms heterologous signaling protein complexes with ATF2 (Y. Sano, et al., *J Biol Chem,* 273(44):29098–105, 1998) and the activity of ATF2 is enhanced after phosphorylation occurs with c-Jun N-terminal kinase. Recent evidence also suggests that linkage between ATF2 and c-Jun is important in expression of cyclin kD1, a gene of critical importance in breast tumors where over-expression of cyclin D1 gene has been implicated (R. Lee, et al., *J Biol Chem,* 274(11):7341–50, 1999).

c-Jun also forms a complex with CREB. This protein complex plays a particularly important role in TNFα gene expression. $TNF_\alpha$ expression has been implicated in endotoxic shock, multiple sclerosis, cerebral malaria and other inflammatory diseases (Delgado-M, Munoz-Elias-Ej, Kan-Y, Gozes-I, Fridkin-M, Brenneman-D E, Gomariz-R P, Ganea-D, *J-Biol-Chem* 273(47):31427–36,1998). The complex CREB/c-Jun has also been implicated in squamous cell differentiation and plays a role in transglutaminase I activity in tracheal epithelial cells (A. Medvedev, et al., *J Biol Chem,* 274(6):3887–96, 1999).

Another example of a c-Jun complex associated with disease is the Nrf1 complex with c-Jun. The Nrf1/c-Jun complex is associated with signaling by the $TNF_\alpha$ promoter in stimulated mast cells (V. Novotny, et al., *Nucleic Acids Res,* 26(23):5480–5, 1998).

Accordingly, in view of the numerous combinations in which c-Jun participates, there is a need in the art to achieve a better understanding of the mechanism by which c-Jun and complexes of c-Jun with signaling proteins contribute to fibrotic proliferative disorders and for methods of treatment of such diseases.

BRIEF DESCRIPTION OF THE INVENTION

The present invention is based upon the discovery that complexes containing activated (i.e. phosphorylated) c-Jun function as signaling entities in connection with fibrotic proliferative disorders. It has further been discovered that compounds that block the activity of c-Jun kinase, the enzyme active in phosphorylation of c-Jun, are effective in modulating the phosphorylation of c-Jun and, hence, of the formation of such c-Jun complexes.

Accordingly, in accordance with the present invention, there are provided methods for treatment of a subject afflicted with a disease or condition characterized by one or more of the following symptoms:

increased levels of c-Jun homodimers, increased heterodimerization of c-Jun with another signaling peptide, increased levels of phosphorylated c-Jun, and increased presence of Jun kinase.

The invention treatment method comprises administering to the subject an amount of a compound effective to ameliorate one or more of the symptoms of the disease or condition. Such diseases and conditions are often further characterized by the presence of one or more of the following additional symptoms:

increased levels of PDGF, increased levels of c-Jun, activation of NF-kappaB or NF-kappaB p65, neutrophil infiltration, and elevated levels of inflammatory cytokine(s).

Exemplary compounds suitable for use in the invention treatment methods are generally antifibrotic and/or antiproliferative agents, with the most preferred compounds being pentoxifylline and functional derivatives or metabolites thereof, such as 1-(5-oxohexyl)-3,7-dimethylxanthine (pentoxifylline), 1-(5-hydroxyhexyl)-3,7-dimethylxanthine (metabolite-1), propentofylline, and the like, and combinations of any two or more thereof. In addition, antisense c-Jun kinase is also contemplated for treatment of fibrotic proliferative disorders according to the present invention because c-Jun kinase facilitates phosphorylation of c-Jun at serine 73, which produces activated c-Jun having the ability to form homodimers and heterodimers with other signaling peptides.

In another embodiment according to the present invention, there are provided assay(s) for identifying whether a test compound is useful for treatment of a subject afflicted with a fibroproliferative disease. The invention assay(s) comprise determining the levels of Jun kinase activity in the presence and absence of the test compound in test cells maintained in the presence of serum obtained from a subject afflicted with a fibroproliferative disease.

In another embodiment according to the present invention, there are provided in vitro assay(s) for identifying whether a test compound that reduces c-Jun phosphorylation is likely to be effective for treatment of a subject afflicted with a fibroproliferative disease. Invention in vitro assay(s) comprise determining the uptake by test cells in suitable media therefor, of a labeled building block indicative of cell proliferation, wherein said uptake is determined in the presence of serum obtained from a subject afflicted with a fibroproliferative disease, and in the presence and absence of the test compound. A reduction of uptake by the test cells of the labeled building block in the presence of the test compound, relative to the uptake by test cells of the labeled building block in the absence of the test compound, is predictive of the efficacy of the test compound for the treatment of diseases or conditions according to the invention treatment methods. The fibroproliferative activity of a test drug can be measured using a variety of known procedures, for example, the modification of tritiated thymidine uptake can be measured using the method of Dohlman et al. in *Immunol.* 52:577–584 (1984) and normal human skin fibroblasts as reported by Peterson (see *Hepatol.* 15(2):191–197, 1992).

Test cells useful in the practice of either of the invention in vitro assay(s) include fibroblasts, neuroblastomas, glial cells, smooth muscle cells, cells obtained from the particular organ of interest, and the like, and combinations of any two or more thereof.

In another embodiment according to the present invention, there are provided kit(s) useful for assays to determine whether a test compound is likely to be effective for treatment of diseases and/or conditions characterized by:

increased levels of c-Jun homodimers, increased heterodimerization of c-Jun with another signaling peptide, increased levels of phosphorylated c-Jun, and increased presence of Jun kinase.

The invention kit(s) comprise:

cultured fibroblasts, glial cells, smooth muscle cells, or cells obtained from the particular organ of interest in suitable assay medium, a composition containing a predetermined concentration of c-Jun, and one or more labeled building blocks indicative of cell proliferation.

DETAILED DESCRIPTION OF THE INVENTION

Figure 1:
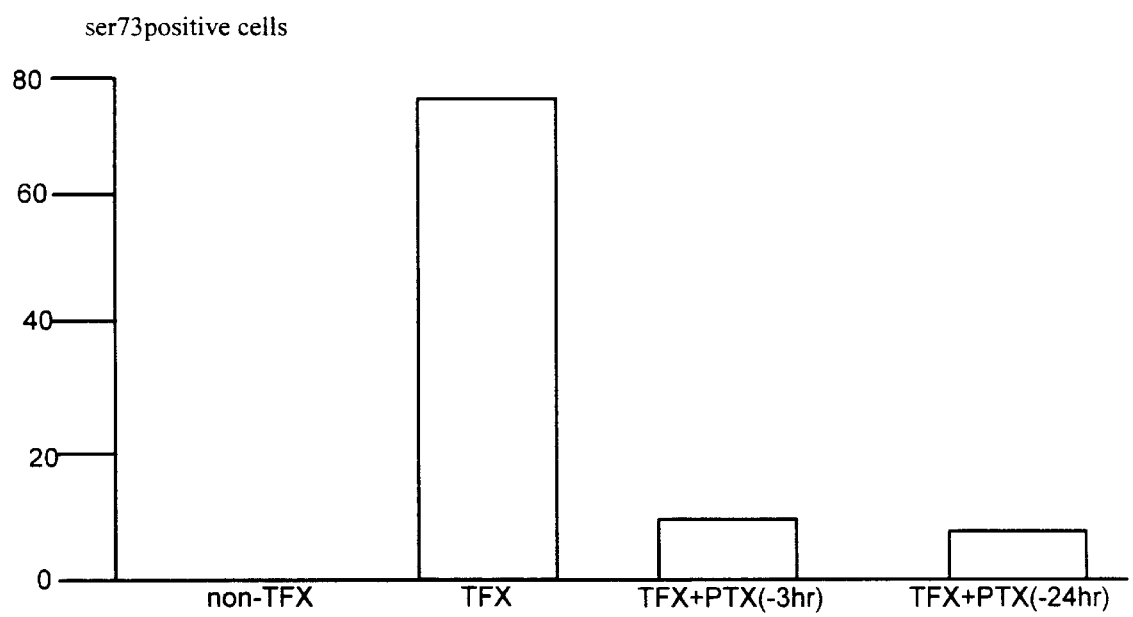
FIG. 1 is a graph showing the effect of pentoxifylline on immunoreactivity dependent on phosphorylation of c-Jun at serine 73 in PC12ES cells transfected with wild type c-Jun gene. Non-TFX=non-transfected cells (control); TFX= transfected cells without pentoxifylline treatment; TFX+ PTX (−3 hr)=cells treated with 3.5-mM pentoxifylline 3 hours prior to transfection; TFX+PTX (−24 hr)=cells treated with 3.5-mM pentoxifylline 24 hours prior to transfection. The ordinate represents the number of ser 73 positive cells per field.

In accordance with the present invention, there are provided methods for treatment of a subject afflicted with a disease or condition characterized by one or more of the following symptoms:

increased levels of c-Jun homodimers, increased heterodimerization of c-Jun with another signaling peptide, increased levels of phosphorylated c-Jun, and increased presence of Jun kinase.

The invention treatment method comprises administering to the subject an amount of a compound effective to ameliorate one or more of the symptoms of the disease or condition. Such diseases and conditions are often further characterized by the presence of one or more of the following additional symptoms:

increased levels of PDGF, activation of NF-kappaB or NF-kappaB p65, neutrophil infiltration, and increased levels of inflammatory cytokine(s).

For example, the additional symptoms can include an increased level of tumor necrosis factor (TNF), interleukin-1 (IL-1), interleukin-4 (IL-4), interleukin-12 (IL-12), insulin growth factor-1 (IGF-1), insulin growth factor-2 (IGF-2), TGF-alpha, TGF-beta, epidermal growth factor (EGF), nerve growth factor (NGF), acidic fibroblast growth factor (aFGF), basic fibroblast growth factor (bFGF), and the like.

Compounds useful in the practice of invention treatment methods are a diverse group of drugs that have been implicated as having a role for the treatment of fibrotic and proliferative diseases and are referred to herein as "antifibrotic and/or antiproliferative agents." For example, antifibrotic and/or antiproliferative agents that are useful in practice of the invention methods include such compounds as hydrocortizone (P. J. Bray, et al., *Biomed Pharmacother,* 52(6): 259–63, 1998), Losartin (N. Varo, et al., *J Hypertens,* 17(1): 107–14, 1999 and H. Peters, et al., *Kidney Int.* 54(5)(:445–50, 1998), Pirfenidone (G. Raghu, et al., *Am J Respir Crit Care Med,* 159(4Pt 1):1061–9, 1999; S. N. Iyer, et al., *J Pharmacol Exp Ther,* 289(1):211–8, 1999;; G. Gurujeyalakshmi, et al., *Am J Physiol,* 276(2 Pt 1):L311–8, 1999; A. K. Dosanjh, et al., *Transplant Proc,* 30(5):1910–1, 1998; B. S. Lee, et al., *J Clin Endocrinol Metab,* 83(1):219–23, 1998; and S. N. Iyer, et al., *Exp Lung Res,* 24(1):119–32, 1998; these investigators studied prifenidone as an antifibrotic/antiproliferative agent in hepatic fibrosis, uterine leiomyomas, obliterative bronchiolitis and other forms of lung fibrosis), nitric oxide (H. Trachtman, et al., *J Investig Med*, 47(3):114–20, 1999), isoniazid or conjugated-isoniazid (P. N. Filimonov, et al., *Probl Tuberk*,(1):63–5, 1999), halofuginone (A. Nagler, et al.,*Am J Obstet Gynecol*, 180(3 Pt 1):558–63, 1999; M. Pines, et al., *Gen Pharmacol*, 30(4):445–50, 1998 and A. Nagler, et al., *Ann Surg*, 227(4):575–82, 1998), TGF$_\beta$ RII/FC (Y. Isaka, et al.,*Kidney Int*, 55(2):465–75, 1999), an angiotensin converting enzyme inhibitor (F. J. Villarreal, et al., *Basic Res Cardiol*, 93 Suppl 3:4–7, 1998 and J. J. Morrissey, et al., *Am J Physiol*, 276(1 Pt 2):F39045, 1999), angiotensin II, and angiotensin I receptor antagonist (Morrissey and Klahr, supra, 1999), enalapril (Peters, et al., supra, 1998), Octreotide (J. Fort, et al., *Hepatology*, 28(6):1525–31, 1998; and S. S. Mansy, et al., Arzneimittelforschung, 48(8):855–61, 1998), silyburn marianum, picrohiza kurroa (S. Luper, *Altern Med Rev*, 3(6):410–21, 1998), captopril (B. D. Uhal, et al., *Am J Physiol*, 275(5 Pt 1)L013–7, 1998), terbinafine (Ricard-Blum, et al., *Eur J Clin Invest*, 28(9):748–54, 1998), a combination of pentoxifylline and tocopherol S. Delanjan, *Br J Radiol*, 71(848):892–4, 1998), glycyrrhizin (J. Y. Wang, et al., *Liver*, 18(3):180–5, 1998), interferon-α (Fort, et al., supra, 1998; J. Fort, et al., *J Hepatol*, 29(2):263–70, 1998, phosphatidyl choline (P. Cales, *Biomed Phaarmacother*, 52(6):259–63, 1998), colchicine (A. Floreani, et al.,*Aliment Pharmacol Ther*, 12(7):653–6, 1998), tetrandrine (F. Chen, et al., *Biochem Biopys Res Commun*, 231(1):99–102, 1997 and F. Chen, et al., *Ann Clin Lab Sci*, 28(1)1–13, 1998), tenidap (O. Sanchez-Pernaute, et al., *Arthritis Rheum*, 40(12):214–56, 1997), decorin (S. N. Giri, et al., *Biochem Pharmacol*, 54(11):1205–16, 1997), pentifylline (S. Saika, et al., *Ophthalmic Res*, 28(3):165–70, 1996), acanthoic acid (H. S. Kang, et al., *Cell Immunol*, 170(2):212–21, 1996), polyenylphosphatidylcholine (X, Ma, et al., *J Hepatol*, 24(5):604–13, 1996), a combination of taurine and niacin (G. Gurujeyalaksmi, et al., *J Pharmacol Exp Ther*, 277(2):1152–7, 1996), or combinations of any two or more thereof.

Preferred compounds for use in practice of the invention method block c-Jun phosphorylation, inhibit Jun kinase, or inhibit c-Jun kinase kinase. Such compounds include 1-(5-oxohexyl)-3,7-dimethylxanthine(pentoxifylline), and oxidation-, reduction-, substitution- and/or rearrangement-products thereof, such as, for example, metabolite-1 through metabolite-7 as described by Luke and Rocci in *J Chromatogr*. 374(1):191–195 (1986) (e.g., 1-(5-hydroxyhexyl)-3,7-dimethyl-xanthine(metabolite-1)), as well as synthetic variants thereof (e.g., propentofylline).

Additional compounds that block c-Jun phosphorylation or inhibit Jun kinase include JNK interacting protein-1 (JIP-1) ((Lee, et al, supra, 1999), glutathione S-transferase Pi (GSTp) (V. Adler, et al.,*EMBO J,* 18(5):1321–34, 1999), islet-brain 1 (IB-1) (C. Bonny, et al., *J Biol Chem,* 273(4):1843–6, 1998), specific JNK inhibitor (S. Amar, et al., *Cancer Chemother Pharmacol,* 41(1):79–85, 1997), mitogen activated protein kinase phosphatase-1 (MKP-1) (K. R. Laderoute, et al.,*J Biol Chem,* 274(18):12890–7, 1999) and JNK inhibitor KT7515 (Cedarlane), Ontario, Canada.

An additional class of compounds that are effective to reduce the level of phosphorylated c-Jun are c-Jun antisense oligonucleotides. For example, an antisense phosphothioate analog of the oligonucleotides to the 5' end of c-jun (obtained from Genesys) useful to block production of c-Jun has the following sequence:
SEQ ID NO:1

5'-GCAGTCATAGAACAGTCCGTCACTTCACGT-3'
When F8 cells were incubated with the c-jun antisense oligonucleotide (SEQ ID NO:1) for twenty-four hours prior to treatment with PDGF to stimulate production of c-Jun protein, a substantially decreased amount of c-Jun protein was produced by the cells compared with the level produced in cells that were not pretreated with the c-jun antisense oligonucleotide. Since the level of c-Jun protein was decreased by the c-jun antisense oligonucleotide, there follows a decreased level of phosphorylated c-Jun as well.

Representative fibroproliferative conditions and diseases characterized by the above symptoms and that can be beneficially treated according to the invention treatment methods include interstitial lung disease, human fibrotic lung disease (e.g., idiopathic pulmonary fibrosis (IPF), adult respiratory distress syndrome (ARDS), tumor stroma in lung disease, systemic sclerosis, Hermansky-Pudlak syndrome (HPS), coal worker's pneumoconiosis (CWP), chronic pulmonary hypertension, AIDS associated pulmonary hypertension, and the like), human kidney disease (e.g., nephrotic syndrome, Alport's syndrome, HIV-associated nephropathy, polycystic kidney disease, Fabry's disease, diabetic nephropathy, and the like), glomerular nephritis, nephritis associated with systemic lupus, peritoneal fibrosis, liver fibrosis, myocardial fibrosis, pulmonary fibrosis, Grave's ophthalmopathy, drug induced ergotism, cardiovascular disease, cancer (including desmoid tumor), Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, gynecological cancer (e.g., ovarian cancer, Lynch syndrome, and the like), Kaposi's sarcoma, Hansen's disease, inflammatory bowel disease (including stricture formation in Crohn's disease and microscopic colitis), and the like.

As employed herein, reference to "increased levels of" a naturally occurring substance in a subject means any level that is significantly higher than levels that are considered to be normal.

As employed herein, the term "PDGF" means platelet derived growth factors and embraces species such as PDGF-AA, PDGF-BB, PDGF-AB, and the like.

As employed herein, the phrase "inflammatory cytokine (s)" embraces such cytokines as tumor necrosis factor (TNF), interleukin-1 (IL-1), interleukin-4 (IL-4), interleukin-12 (IL-12), insulin growth factor-1 (IGF-1), insulin growth factor-2 (IGF-2), TGF-alpha, TGF-beta, epidermal growth factor (EGF), nerve growth factor (NGF), acidic fibroblast growth factor (aFGF), basic fibroblast growth factor (bFGF), and the like.

The active components described for use herein can be delivered in a suitable vehicle, thereby rendering such compositions amenable to oral delivery, transdermal delivery, subcutaneous delivery (e.g., intravenous delivery, intramuscular delivery, intraarterial delivery, intraperitoneal delivery, and the like), topical delivery, inhalation delivery, osmotic pump, and the like.

Depending on the mode of delivery employed, the above-described compositions can be delivered in a variety of pharmaceutically acceptable forms. For example, the above-described compositions can be delivered in the form of a solid, solution, emulsion, dispersion, micelle, liposome, and the like.

Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. The active compounds contemplated for use herein are included in the pharmaceutical composition in an amount sufficient to produce the desired effect upon the target process, condition or disease.

Pharmaceutical compositions containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions. In addition, such compositions may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. Tablets, and the like, may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical compositions may also be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like, can be incorporated as required.

Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In addition, sustained release systems, including semi-permeable polymer matrices in the form of shaped articles (e.g., films or microcapsules) can also be used for the administration of the active compound employed herein. Sustained release pentoxifylline compositions also include liposomally entrapped pentoxifylline.

Since individual subjects may present a wide variation in severity of symptoms and each active ingredient has its unique therapeutic characteristics, it is up to the practitioner to determine a subject's response to treatment and vary the dosages accordingly. For example, effective pentoxifylline levels for a given patient can readily be achieved by monitoring the patient using commonly available techniques, such as, for example, by subjecting serum obtained from the patient to high performance liquid chromatography (HPLC). The practitioner can then determine whether increased or decreased dosages of pentoxifylline are indicated, based on the level detected in the patient's serum.

Typical daily doses of the active component, in general, lie within the range of from about 10 $\mu$g up to about 100 mg per kg body weight, and, preferably within the range of from about 50 $\mu$g up to about 50 mg per kg body weight and can be administered up to four times daily. The daily dose lies within the range of from about 1 $\mu$g to about 100 mg per kg body weight, and, preferably, within the range of from 10 $\mu$g to 10 mg per kg body weight. Where one will operate within the above ranges will vary based on a variety of considerations, such as, for example, the age of the patient, the size of the patient, what other medications, if any, the patient may be taking (especially steroids), and the like.

As readily recognized by those of skill in the art, the active compounds contemplated for use herein can be administered as part of a slow release formulation, as a single bolus for rapid administration, as part of a depot formulation, as part of a nutritional supplement, and the like.

In another aspect of the present invention, a combination treating agent can be employed for the treatment of diseases and/or conditions characterized by elevated levels of such factors as increased levels of c-Jun, increased levels of c-Jun homodimers, increased heterodimerization of c-Jun with another signaling peptide, and the like, wherein kinase inhibitors are combined with "an antifibrotic and/or antiproliferative agent" as described herein. Those of skill in the art can readily identify a variety of kinase inhibitors suitable for this purpose. Presently preferred kinase inhibitors include cyclic AMP-dependent kinase inhibitors, JNK inhibitors, and the like. Examples of kinase inhibitors include H7, staurosporine, genistein, SP-203580, PD98059, and the like.

In another aspect of the present invention, a combination treating agent can be employed for the treatment of diseases and/or conditions characterized by elevated levels of such factors as increased levels of c-Jun, increased levels of c-Jun homodimers, increased heterodimerization of c-Jun with another signaling peptide, and the like, wherein "an antifibrotic and/or antiproliferative agent" as described herein is combined with an inhibitor of cytochrome P-450, particularly cytochrome P-4501A2 (CYP1A2). Examples of CYP1A2 inhibitors include ciprofloxacin and furafylline, both of which have been shown to inhibit the metabolism of pentoxifylline and thus potentiate the effect of pentoxifylline and its metabolite-1.

Jun kinase controls the activity of c-jun, which then complexes with c-fos to make the AP-1 transcription factor. Homodimers of the jun protein product or heterodimeric complexes of jun-fos form the AP-1 nuclear transcription factor which controls the expression of genes possessing this regulatory element, including genes involved in proliferation (see, for example, Schafer et al., supra, 1996) and Bamberger et al., supra, 1996).

In accordance with another embodiment of the present invention, there are provided in vitro assay(s) for identifying whether a test compound is useful for treatment of a subject afflicted with a fibroproliferative disease. The invention assay method comprises determining the levels of Jun kinase activity in the presence and absence of the test compound in test cells maintained in the presence of serum obtained from the subject. A reduction of Jun kinase activity in the presence of the test compound, compared to the absence of the test compound, is predictive of the efficacy of the test compound for use in the invention treatment methods (i.e., in the treatment of diseases or conditions characterized by increased levels of c-Jun homodimers, increased heterodimerization of c-Jun with another signaling peptide, increased levels of phosphorylated c-Jun, increased presence of Jun kinase, and the like).

In accordance with another embodiment of the present invention, there are provided in vitro assay(s) to determine whether a compound that reduces c-Jun phosphorylation is likely to be effective for treatment of a subject afflicted with a fibroproliferative disease. In this embodiment, the assay method comprises determining the uptake by test cells in suitable media therefor, of a labeled building block indicative of cell proliferation, wherein the uptake is determined in the presence of serum obtained from the subject, and in the presence and absence of the compound. A reduction of uptake by the test cells of labeled building block in the presence of the test compound, relative to the uptake by the test cells of labeled building block in the absence of the test compound, is predictive of the efficacy of the test compound for use in the invention treatment methods.

As employed herein, the phrase "labeled building block" refers to any compound which is taken up by DNA during active DNA synthesis, wherein such compound can be readily detected by any suitable means. Such labeled materials can be rendered detectable by a variety of means, e.g., as a result of radioactive labeling, by colorimetric detection, and the like. Examples of suitable labeled building blocks contemplated for use herein include tritiated thymidine, bromouridine, and the like.

Test cells suitable for use in either of the above-described invention assay(s) include fibroblasts, neuroblastomas, glial cells, smooth muscle cells, or cells obtained from the particular organ that is the disease target, e.g., liver myofibroblasts are useful to test sera samples from liver fibrosis patients, pulmonary fibroblasts or smooth muscle cells (mesenchymal cells) are useful to test sera samples from pulmonary fibrosis patients, glial cells are useful to test sera samples from Alzheimer's patients, intestinal fibroblasts and intestinal smooth muscle cells are useful to test sera samples from patients with inflammatory bowel disease, and the like. Other test cells contemplated for use herein include cultured human skin fibroblasts, vascular smooth muscle cells, mesangial cells (kidney), hematopoietic cells (leukemias), Kaposi sarcoma-derived cells (Kaposi sarcoma), epithelial cells, and the like. Preferably the test cells are prepared for use in the invention assays by transfection with a wild type c-jun gene using known methods.

As readily recognized by those of skill in the art, suitable media appropriate for use with a test cell will depend on the particular test cell being employed. Those of skill in the art can readily determine appropriate media to employ once the test cell of choice has been identified.

In accordance with yet another embodiment of the present invention, there are provided kits useful for assays to determine whether a test compound is likely to be effective for treatment of diseases and/or conditions characterized by one or more of the following:
   increased levels of c-Jun homodimers,
   increased heterodimerization of c-Jun with another signaling peptide,
   increased levels of phosphorylated c-Jun, and
   increased presence of Jun kinase.
The invention kits comprise:
   cultured fibroblasts, glial cells, smooth muscle cells, or cells obtained from the particular organ of interest in suitable assay medium,
   a composition containing a predetermined concentration of c-Jun for use as a control, and
   one or more labeled building block indicative of cell proliferation.
Preferred cultured cells for inclusion in the invention kits are human skin fibroblasts, intestinal smooth muscle cells, liver myofibroblasts, pulmonary fibroblasts, mesenchymal cells, glial cells, intestinal fibroblasts, intestinal smooth muscle cells, vascular smooth muscle cells, mesangial cells, hematopoietic cells, Kaposi sarcoma-derived cells, epithelial cells, and the like.

To determine the mechanism of action of pentoxifylline, studies described in the Examples herein were conducted to determine whether modification of c-jun gene transcription by PDGF and pentoxifylline extended beyond gene expression to protein translation. In these studies, the effect of pentoxifylline and PDGF on c-Jun immunoreactivity in cells treated with PDGF and in cells that were transfected with wild type c-jun plasmid was observed. Three cell types were studied: human fibroblast (F8 cells), human neuroblastoma cells, SKNSH cells, and rat PC12ES cells.

Immunocytochemistry was carried out as described in the Examples herein using antibody to c-Jun and also using antibody to a serine 73 phospho specific c-Jun. Using this serine 73 phospho specific c-Jun antibody, it was determined that pentoxifylline altered the phosphorylation of c-Jun. Treatment of human fibroblast cells with PDGF (8 ng/ml) effectively increased the immunocytochemical staining for c-Jun and also increased the immunocyto-chemical staining for serine 73 phosphorylated c-Jun. By contrast, when the cells were pretreated with pentoxifylline (3.5 mM) prior to transfection, the level of serine 73 phosphorylated c-Jun produced was decreased. These results suggest that pentoxifylline exerts its effect by blocking the phosphorylation of c-Jun on serine 73.

The reduction in phosphorylated c-Jun immunoreactivity by pentoxifylline indicates that pentoxifylline and other compounds that decrease the phosphorylation (i.e., activation) of the c-Jun protein via a block of Jun kinase or otherwise interfere with formation of c-Jun dimers (i.e., homodimers or heterodimers with another signaling peptide) reduce the amount of activated c-Jun that is available to contribute to fibroproliferative disease downstream.

Many fibroproliferative diseases are known to be associated with formation of c-Jun homodimers or heterodimerization of c-Jun with another signaling peptide. For example, it is well accepted that the signalling protein ATF2 forms heterologous signalling protein combinations with c-Jun (Sano et al., supra, 1998) and it is well established that the activity of ATF2 is enhanced after phosphorylation occurs with Jun kinase (c-jun N-terminal kinase). Thus, a decrease in phosphorylation by c-jun N-terminal kinase would ultimately reduce the activity of the ATF2/c-Jun complex. The ATF2/c-Jun complex plays a critical role in TGFβ signaling. It has been reported that TGFβ signals through SMAD and TAK1 pathways which have ATF2 as a common nuclear target. This nuclear target then complexes with c-Jun to ultimately produce the downstream effect of TGFβ signalling (Y. Sano, et al., *J Biol Chem,* 274(13):8949–57, 1999). Thus, a decrease in activity of the ATF2/c-Jun complex would ultimately affect TGF signalling.

Recent evidence also suggests that linkage between ATF2 and c-jun is important in cyclin D1 gene expression, a gene of critical importance in breast tumours where over-expression of cyclin D1 gene has been implicated (Lee, et al., supra, 1999). Thus a downregulation of c-Jun phosphorylation could ultimately affect the ATF2/c-Jun complex and block or inhibit induction of the cyclin D1 gene, which requires c-Jun N-terminal kinase phosphorylation of c-Jun for optimal induction.

Like CREB, (Novotny, et al., *Nucleic Acids Res,* 26(23):5480–5, 1998) also complexes with c-Jun. Thus, a block of c-Jun would block events signalled by the TNFα promoter (through this complex) in stimulated mast cells, which has been implicated in fibrotic diseases, such as hepatitis C.

Another example of the effect of c-Jun heterodimers on disease formation is the complex formed with CREB and c-Jun. This protein complex plays a particularly important role in TNFα gene expression, which has been implicated in endotoxic shock, multiple sclerosis, cerebral malaria, and other inflammatory diseases (Delgado, et al., supra, 1998). Thus, a down regulation in c-Jun phosphorylation would ultimately affect the CREB-Jun complex and thereby downregulate TNFα gene expression. The complex CREB/c-Jun has also been implicated in squamous cell differentiation and plays a critical role in transglutaminase I (TGase I) activity in tracheal epithelial cells (Medvedev, et al., supra, 1999). Thus, a downregulation in c-Jun phosphorylation would reduce levels of the CREB/c-Jun protein, block or inhibit TGase I activity, and ultimately inhibit squamous cell differentiation in carcinoma. These results also suggest a broader role for pentoxifylline (and other inhibitors of c-Jun phosphorylation) in blocking or inhibiting cell differentiation. This would have application in many neoplastic diseases (cancers) and in early stages of fibrosis (i.e., when a constitutive cell differentiates into a fibrotic cell).

The invention will now be described in greater detail by reference to the following non-limiting examples.

EXAMPLE 1

Fibroproliferative activity of sera (500 μl) was assessed by tritiated thymidine uptake using cultured human skin fibroblasts and/or intestinal smooth muscle cells (ATCC). Pentoxifylline (Sigma Chemical Company, St. Louis, Mo.) was tested at 240 μM. MCM was prepared from peripheral blood (10 ml) as has previously been described (see Peterson, et al., supra, 1992).

To assess fibroproliferative activity, medium was removed by aspiration from flasks containing confluent intestinal smooth muscle cells or monolayers of human fibroblasts (at passage 5 to 12). The cells were briefly rinsed with 10–20 ml of sterile saline to remove any remaining medium. Fibroblasts were removed from the flasks by the addition of 5 ml trypsin-EDTA (Gibco, Ontario, Canada) for 30 seconds with gentle rocking at room temperature, followed by pouring off of most of the trypsin solution and incubation at 3° C. for 3–5 minutes.

Cells were resuspended in 10 ml Dulbecco's (DBE, Gibco, Canada), antibiotic/antimycotic (Gibco, Canada) and 0.5% CPSR-2 (Sigma Chemical Co., St. Louis, Mo.), a serum replacement (control processed serum replacement-2) that has low mitogenic activity. Two hundred microliter aliquots of cell suspension ($8 \times 10^3$ cells) are added to 0.32 $cm^2$ flat bottom wells of 96 well microtiter plates and incubated for 24 hours at 3° C. in 5% $CO_2$ in air. The media were removed from each well by aspiration, replaced by 200 μl of DBE supplemented with factors incubated as above for a further 22 hours.

PDGF A/B, (R&D Systems Inc. Minneapolis, Minn.) 8 ng/ml was used as the positive control to stimulate proliferation of fibroblasts in the presence or absence of pentoxifylline (Sigma Chemical Co., St. Louis, Mo.).

Methyl-$^3$H-thymidine 0.5 μCi (Amersham, Ontario, Canada) was added to each well and the incubation continued for an additional 2 hours. To harvest the fibroblasts, the medium was removed by aspiration and replaced by 100 μl of trypsin-EDTA for a few minutes at 37° C. This trypsinization was verified as sufficient to detach all fibroblasts. The loose fibroblasts were then aspirated onto glass fiber filters using a Brandel Cell Harvester (Xymotech Biosystems, Ontario, Canada), washed 8–10 times with phosphate buffered saline, and the radioactivity determined by liquid scintillation. All samples were tested in quadruplicate. The $^3$H-thymidine uptake assay has been verified as a good measure of proliferation of fibroblasts, in response to stimuli or inhibitors, by manual cell counts and MTT assay.

The results produce a fibrogenic stimulation index (FSI), previously called a patient disease index (PDI), and a drug inhibition index (DII), previously called a sensitivity index (DSI).

EXAMPLE 2

Fibroproliferation

The fibroproliferative activity of PDGF was assessed by modification of the tritiated thymidine incorporation method of Dohlman et al. in *Immunol.* 52:577–584 (1984) using normal human skin fibroblasts as reported by Peterson (see *Hepatol.* 15(2):191–197 1992). Briefly, cells were resuspended in Dulbecco's (DBE, Gibco, Canada), antibiotic/antimycotic (Aa, Gibco, Canada) and 0.5% CPSR-2 (Sigma Chemical Co., St. Louis, Mo.), a serum replacement (control processed serum replacement-2) that has low mitogenic activity. Two hundred microliter aliquots of cell suspension ($8 \times 10^3$ cells) were added to 0.32 $cm^2$ flat bottom wells of 96 well microtiter plates and incubated for 24 hours at 3° C. in 5% $CO_2$ in air. The media were replaced by 200 μl of DBE supplemented with factors incubated as above for a further 22 hours. PDGF B/B, (R&D Systems Inc. CA) 8 ng/ml was used to stimulate proliferation of fibroblasts in the presence or absence of pentoxifylline (Sigma Chemical Co., St. Louis, Mo.).

Monocyte conditioned medium (MCM) was prepared from monocytes obtained from patients with liver disease, as previously described by Peterson in *Hepatol.* 15(2): 191–197, 1992). Samples were assessed for their ability to stimulate fibroproliferation and also assessed for the effect of pentoxifylline on that proliferative effect. Methyl-$^3$H-thymidine 0.5 µCi (Amersham Canada) was added to each well, incubated for an additional 2 hours, and then the cells were harvested by aspiration onto glass filters using a Brandel Cell Harvester (Xymotech Biosystems, Ontario, Canada) and the radioactivity was determined by liquid scintillation. All samples were tested in quadruplicate. The $^3$H-thymidine uptake assay has been validated by manual cell counts and MTT assay as a measure of fibroblast number following treatment with either proliferative or antiproliferative agents (see, for example, Peterson et al., in *Immunopharmacol.* 28:259–270, 1994) and Denizat & Lang, in *Immunol. Methods* 89:271–277, 1986), which is incorporated herein by reference in its entirety.

EXAMPLE 3

Determination of c-Jun Phosphorylation in Cells

Human dermal fibroblasts (F8 cells) were plated onto 96 well plates at a density of 8,000 cells per well in Dulbecco's modified eagle media supplemented with 5% fetal calf serum. After twenty-four hours, the media was changed to Dulbecco's modified eagle media supplemented with 0.5% fetal calf serum. Following this incubation, control cells were treated with PDGF (8 ng/ml) for two hours, but test cells were incubated with pentoxifylline (3.5 mM) for three hours or twenty-four hours prior to treatment with the same concentration of PDGF for two hours. The cells were then fixed with paraformaldehyde (4%), washed extensively with phosphate buffered saline, and incubated overnight with a c-Jun specific antibody or a serine 73 phospho specific c-Jun antibody (New England Biolabs) using 50 µl per well of a 1:500 dilution. After the overnight incubation, the primary antibody was removed, and cells were washed, and incubated with secondary antibody overnight for detection. After overnight incubation with the secondary antibody, the cells were washed and incubated with extrAVIDIN peroxidase (1:250; 50 1 per well, Sigma) for two hours prior to addition of the chromagen diaminobenzidine (DAB).

The results of these tests showed that PDGF effectively increased the immunocytochemical staining for c-Jun and also increased the immunocytochemical staining for serine 73 phosphorylated c-Jun. However, pretreatment with pentoxifylline reduced the immunoreactivity of the serine 73 phosphorylated c-Jun, indicating that pentoxifylline inhibits the activation of c-Jun to phosphorylated c-Jun.

EXAMPLE 4

Determination of c-Jun Phosphorylation in c-jun Transfected Cells

Immunoreactivity studies were also conducted in transfected cells to determine the effect of pentoxifylline on phosphorylation of c-Jun. For the transfection experiments all of the test cell types (i.e., human fibroblast, PC12ES, and SKNSH cells) were transfected with a plasmid carrying a wild type c-jun gene (or mutant c-jun gene whose gene product could not be phosphorylated in ser-73) and a CMV promoter (X. U. Ruian et al., submitted to *Neuroscience*, 1999) to ensure high expression of c-jun and translation of c-Jun in these cell types following twenty-four hour incubation.

Immunocytochemical staining for c-Jun in the human fibroblast F8 cells following transfection with a c-jun carrying plasmid was tested using the above antibody specific to a serine 73 phosphorylated c-Jun protein and the immunocytochemical methods described in Example 3 above. The results of these immunoreactivity tests showed elevated levels of serine 73 phosphorylated c-Jun protein was present in the transfected cells.

In further tests, the ability of pentoxifylline to modify the phosphorylation of c-Jun protein was studied by immunocytochemical staining for c-Jun in PC12ES cells that had been transfected with the wild type c-jun plasmid to enhance the expression of c-Jun. Results of these tests shown in FIG. 1, indicate that transfection with wild type c-jun plasmid also sharply increased the serine 73 phosphorylated c-Jun immunoreactivity compared to controls. In fact, the c-Jun positive immunoreactivity was higher in the transfected PC12ES cells than in the transfected F8 cells (an effect probably related to the higher cell turnover during the twenty-four hour transfection period). However, in cells treated with 3.5 mM pentoxifylline for 3 or 24 hours prior to transfection with the c-jun plasmid, the serine 73 phosphorylated c-Jun immunoreactivity (i.e., the number of ser 73 phosphorylated c-Jun positive cells) was reduced by approximately 80% in wild type c-jun plasmid transfected PC12ES cells. The reduction in phosphorylated c-Jun immunoreactivity by pentoxifylline (FIG. 1) indicates that pentoxifylline decreases the phosphorylated status (i.e., activation) of the c-Jun protein via a block of Jun kinase, therefore reducing the amount of activated c-Jun that is available to have an effect further downstream.

A similar result was obtained when the transfection experiment was repeated using SKNSH cells.

EXAMPLE 5

The effect of c-Jun Antisense on Phosphorylation of c-Jun

The above immunocytochemical staining experiments were repeated in human dermal fibroblasts (F8 cells) using antisense c-jun oligonucleotides according to the method of (Yoshida, et al., (*Molec Cel Biol* 17(7):4014–4023, 1997). The overall method is similar to that described in Example 3 above, except that in the pretreatment step the cells were incubated with c-jun antisense oligonucleotide (SEQ ID NO:1) (10 µM) (obtained from Genesys) for twenty-four hours, and the primary antibody used was specific to c-Jun (PCO6) (Oncogene Science).

The results of these tests indicate that incubation of cells with PDGF (8 ng/ml) for two hours caused a marked positive immunoreactivity with the c-Jun antibody and that this immunoreactivity was significantly reduced by preincubation of cells for twenty-four hours with c-jun antisense. A decrease in the amount of c-Jun is expected to also result in reduction in the amount of phosphorylated c-Jun produced.

While the invention has been described in detail with reference to certain preferred embodiments thereof, it will be understood that modifications and are within the spirit and scope of that which is described and claimed.

That which is claimed is:

1. The method for the treatment of a subject afflicted with a disease or condition characterized by one or more of the following symptoms:
   increased levels of c-Jun homodimers,
   increased heterodimerization of c-Jun with another signaling peptide,
   increased levels of phosphorylated c-Jun, and
   increased presence of Jun kinase,
said method comprising administering to the subject an amount of a compound effective to ameliorate one or more of the symptoms of the disease or condition.

2. The method according to claim 1 wherein the disease is further characterized by one or more of the following:
   elevation of PDGF levels,
   elevation of c-Jun
   activation of NF-kappaB or NF-kappaB p65,
   neutrophil infiltration, or
   elevated levels of inflammatory cytokine(s).

3. The method according to claim 1 wherein said compound is an antifibrotic and/or antiproliferative agent.

4. The method according to claim 3 wherein said compound is hydrocortizone, Losartin, Pirfenidone, nitric oxide, isoniazid or conjugated-isoniazid, halofuginone, TGFβ RII/FC, an angiotensin converting enzyme inhibitor, angiotensin II, an angiotensin 1 receptor antagonist, enalapril, Octreotide, silyburn marianum, picrohiza kurroa, captopril, terbinafine, a combination of pentoxifylline and tocopherol, glycyrrhizin, interferon-a, phosphatidyl choline, colchicine, tetrandrine, tenidap, decorin, pentifylline, acanthoic acid, polyenylphosphatidylcholine, a combination of taurine and niacin, or a combination of any two or more thereof.

5. The method according to claim 1 wherein said compound is pentoxifylline, or a functional derivative or metabolite thereof.

6. The method according to claim 5 wherein said pentoxifylline, or functional derivative or metabolites thereof, is 1-(5-oxohexyl)-3,7-dimethylxanthine (pentoxifylline), 1-(5-hydroxyhexyl)-3,7-dimethylxanthine (metabolite-1), or propentofylline.

7. The method according to claim 1, wherein said compound is a c-Jun antisense.

8. The method according to claim 1 wherein said compound is administered in combination with an inhibitor of cytochrome P-450.

9. The method according to claim 1, wherein said compound is administered in combination with a kinase inhibitor.

10. The method according to claim 3 wherein said compound is co-administered with an inhibitor of a cytochrome P-450.

11. The method according to claim 10 wherein the cytochrome P-450 is cytochrome P-4501A2.

12. The method according to claim 11 wherein the inhibitor of cytochrome P-4501A2 is ciprofloxacin or furafylline.

13. The method according to claim 1 wherein the signaling peptide is CREB.

14. The method according to claim 13 wherein the disease or condition is breast tumor.

15. The method according to claim 13 wherein the disease is further characterized by increased expression of TNF-α.

16. The method according to claim 15 wherein the disease is endotoxic shock, multiple sclerosis, or cerebral malaria.

17. The method according to claim 13 wherein the disease is further associated with a disorder in squamous cell differentiation.

18. The method according to claim 17 wherein the disease is squamous cell carcinoma.

19. The method according to claim 13 wherein the disease is further characterized by fibrosis.

20. The method according to claim 1 herein the signaling peptide is Nrf1.

21. The method according to claim 20 wherein the disease is further characterized by fibrosis.

22. The method according to claim 21 wherein the disease is hepatitis C.

23. The method according to claim 1 wherein the signaling peptide is ATF2.

24. The method according to claim 23 wherein the disease is a cancer.

25. The method according to claim 1 wherein the disease is renal fibrosis, abdominal adhesions, radiation induced fibrosis, obliterative bronchiolitis, silicosis lesions, or Tenon's capsule fibroproliferation.

26. The method according to claim 1 wherein the disease is interstitial lung disease, human fibrotic lung disease, human kidney disease, glomerular nephritis, nephritis associated with systemic lupus, peritoneal fibrosis, liver fibrosis, myocardial fibrosis, pulmonary fibrosis, Grave's ophthalmopathy, drug induced ergotism, cardiovascular disease, cancer, Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, gynecological cancer, Kaposi's sarcoma, Hansen's disease, or inflammatory bowel disease not including collagenous colitis when the compound is pentoxifylline.

27. The method according to claim 1 wherein said compound is delivered orally, transdermally, intravenously, intramuscularly, topically, by inhalation, or rectally.

28. The method according to claim 14 wherein said compound is delivered orally.

29. The method according to claim 1 wherein said compound is administered to the subject by sustained release.

30. The method according to claim 1 wherein said compound is administered to the subject at least two times a day.

31. The method according to claim 1 wherein said compound is administered to the subject at least four times a day.

32. The method according to claim 1, wherein said compound is administered in combination with a kinase inhibitor.

33. The method according to claim 1 further comprising monitoring the level of phosphorylated c-Jun in serum from the subject, and adjusting the dosage of said compound based on the level detected in the serum of the subject.

34. An in vitro assay for identifying whether a test compound is useful for treatment of a subject afflicted with a fibroproliferative disease, said method comprising:

determining the levels of Jun kinase activity in the presence and absence of the test compound in test cells maintained in the presence of serum obtained from the subject, wherein the test cells are fibroblasts, neuroblastomas, glial cells, smooth muscle cells, or cells obtained from the particular organ of interest, and wherein a reduction of Jun kinase activity in the presence of the test compound, compared to the absence of said test compound, is predictive of the efficacy of said test compound for the treatment of diseases or conditions characterized by one or more of the following:

increased levels of c-Jun homodimers, increased heterodimerization of c-Jun with another signaling peptide, increased levels of phosphorylated c-Jun, and increased presence of Jun kinase.

35. An in vitro assay to determine whether a compound that reduces c-Jun phosphorylation is effective for treatment of a subject afflicted with a fibroproliferative disease, said method comprising:

determining the uptake by test cells in suitable media therefor, of a labeled building block indicative of cell proliferation, wherein said uptake is determined in the presence of serum obtained from said subject, and in the presence and absence of said compound, wherein test cells are fibroblasts, glial cells, smooth muscle cells, or cells obtained from the particular organ of interest, and wherein reduction of uptake by the test cells of labeled building block in the presence of said test compound, relative to the uptake by the test cells of labeled building block in the absence of said test compound, is predictive of the efficacy of said test compound for the treatment of diseases or conditions characterized by one or more of the following:

increased levels of c-Jun homodimers, increased heterodimerization of c-Jun with another signaling peptide, increased levels of phosphorylated c-Jun, and increased presence of Jun kinase.

36. An assay according to claim 35 wherein said labeled building block is tritiated thymidine.

37. An assay according to claim 35 wherein said test cells are liver myofibroblasts, pulmonary fibroblasts, smooth muscle cells, mesenchymal cells, glial cells, intestinal fibroblasts, intestinal smooth muscle cells, cultured human skin fibroblasts, vascular smooth muscle cells, mesangial cells, hematopoietic cells, Kaposi sarcoma-derived cells or epithelial cells.

38. An assay according to claim 37 wherein the test cells comprise a monolayer of cultured human skin fibroblasts.

39. An assay according to claim 37 wherein said test cells comprise confluent intestinal smooth muscle cells.

40. A kit useful for assays to determine whether a test compound is effective for treatment of diseases and/or conditions characterized by one or more of the following:

increased levels of c-Jun homodimers, increased heterodimerization of c-Jun with another signaling peptide, increased levels of phosphorylated c-Jun, and increased presence of Jun kinase, said kit comprising:

cultured fibroblasts, glial cells, smooth muscle cells, or cells obtained from the particular organ of interest in suitable assay medium, a composition containing a predetermined concentration of c-Jun, and one or more labeled building block indicative of cell proliferation.

41. A kit according to claim 40 wherein said cultured cells are human skin fibroblasts, intestinal smooth muscle cells, liver myofibroblasts, pulmonary fibroblasts, mesenchymal cells, glial cells, intestinal fibroblasts, intestinal smooth muscle cells, vascular smooth muscle cells, mesangial cells, hematopoietic cells, Kaposi sarcoma-derived cells or epithelial cells.

42. A kit according to claim 40 wherein said labeled building block is tritiated thymidine or bromouridine.

* * * * *

UNITED STATES PATENT AND TRADEMARK OFFICE
CERTIFICATE OF CORRECTION

PATENT NO.     : 6,294,350 B1
DATED          : September 25, 2001
INVENTOR(S)    : Peterson It is certified that error appears in the above-identified patent and that said Letters Patent is hereby corrected as shown below:

<u>Column 15,</u>
Line 47, delete "interferon-a" and insert -- interferon-α --.

<u>Column 16,</u>
Line 42, delete "herein" and insert -- wherein --.

Signed and Sealed this

Twenty-fifth Day of March, 2003

JAMES E. ROGAN
*Director of the United States Patent and Trademark Office*